US009827179B2

(12) United States Patent
Shapiro et al.

(10) Patent No.: US 9,827,179 B2
(45) Date of Patent: Nov. 28, 2017

(54) PERSONAL CLEANSERS AND SURFACTANT BLEND THEREFOR

(71) Applicant: Stepan Company, Northfield, IL (US)

(72) Inventors: Irene Shapiro, Buffalo Grove, IL (US); Dave Allen, Chicago, IL (US); Aaron Brown, Chicago, IL (US)

(73) Assignee: STEPAN COMPANY, Northfield, IL (US)

( * ) Notice: Subject to any disclaimer, the term of this patent is extended or adjusted under 35 U.S.C. 154(b) by 0 days.

(21) Appl. No.: 14/902,616

(22) PCT Filed: Jul. 8, 2014

(86) PCT No.: PCT/US2014/045709
§ 371 (c)(1),
(2) Date: Jan. 4, 2016

(87) PCT Pub. No.: WO2015/006300
PCT Pub. Date: Jan. 15, 2015

(65) Prior Publication Data
US 2016/0175213 A1 Jun. 23, 2016

Related U.S. Application Data

(60) Provisional application No. 61/845,868, filed on Jul. 12, 2013, provisional application No. 61/951,450, filed on Mar. 11, 2014.

(51) Int. Cl.
*A61K 8/42* (2006.01)
*A61Q 5/02* (2006.01)
*A61Q 19/10* (2006.01)

(52) U.S. Cl.
CPC .................. *A61K 8/42* (2013.01); *A61Q 5/02* (2013.01); *A61Q 19/10* (2013.01)

(58) Field of Classification Search
CPC ............. A61K 8/42; A61Q 19/10; A61Q 5/02
See application file for complete search history.

(56) References Cited

U.S. PATENT DOCUMENTS

| 3,417,114 A | 12/1968 | Kuceski |
| 3,676,372 A | 7/1972 | Sharman |
| 3,843,543 A | 10/1974 | Hewitt |
| 3,951,596 A | 4/1976 | Hewitt |
| 4,228,044 A | 10/1980 | Cambre |
| 4,506,051 A | 3/1985 | Rance |
| 6,485,713 B1 | 11/2002 | Bonda et al. |
| 7,790,146 B2 | 9/2010 | Lott et al. |
| 8,053,400 B2 | 11/2011 | Dong et al. |
| 8,153,105 B1 | 4/2012 | Deangelo |
| 2003/0215472 A1 | 11/2003 | Bonda et al. |
| 2006/0154836 A1* | 7/2006 | SenGupta .............. A61K 8/062 510/122 |
| 2010/0183539 A1 | 7/2010 | Bernhardt et al. |
| 2012/0295831 A1* | 11/2012 | Masters ................ C11D 1/521 510/432 |

FOREIGN PATENT DOCUMENTS

| CN | 102920630 A | 2/2013 | |
| JP | 2007063545 A | 3/2007 | |
| WO | 2007/085568 A1 | 8/2007 | |
| WO | WO 2011075642 A1 * | 6/2011 | ............. C11D 1/521 |
| WO | 2011/085310 A1 | 7/2011 | |
| WO | 2012/061094 A1 | 5/2012 | |
| WO | 2013/052545 A1 | 4/2013 | |

OTHER PUBLICATIONS

PCT International Search Report and Written Opinion dated Dec. 1, 2014 in corresponding Application No. PCT/US2014/045709, 18 pages.

* cited by examiner

*Primary Examiner* — Mark V Stevens
(74) *Attorney, Agent, or Firm* — Dilworth IP LLC

(57) ABSTRACT

Personal cleansers and surfactant blends useful therein are disclosed. The cleansers comprise a primary anionic surfactant, a saturated $C_8$-$C_{14}$ alkyl N,N-dialkylamide, and water. The cleansers have good foaming properties and improved viscosity build profiles compared with cleansers that rely on alkanolamides or betaines as the secondary surfactant. The saturated $C_8$-$C_{14}$ alkyl N,N-dialkylamides are water-white liquids that solubilize cleanser components well, including high levels of fragrances, and can be formulated easily without heating at any actives level up to 100%. Importantly, the surfactant blends build viscosity with less added salt compared with alkanolamide or betaine-based blends, even with more challenging anionic surfactants. Moisturizing cleansers disclosed herein have excellent flash foaming character, foam volume, and foam feel and provide a luxurious, lotion-like after-feel. The personal cleansers include, among others, shampoos, body washes, facial cleansers, shower gels, liquid soaps, hand soaps, baby liquid cleansers, pet shampoos, and bubble baths. The fatty N,N-dialkylamides are also valuable for formulating oil-in-water emulsions with good stability.

15 Claims, No Drawings

US 9,827,179 B2

PERSONAL CLEANSERS AND SURFACTANT BLEND THEREFOR

FIELD OF THE INVENTION

The invention relates to personal cleansers and surfactant blends useful therein. The blends impart excellent foaming, mildness, and viscosity build to body washes, shampoos, liquid hand soaps, and other personal cleansers.

BACKGROUND OF THE INVENTION

Personal cleansers delight users with rich lather and a fresh, clean feel for hair and skin. Most personal cleansers—shampoos, body washes, facial cleansers, liquid soaps, and the like—are formulated with a combination of surfactants. A primary anionic surfactant provides cleansing and foaming properties to allow fast, complete removal of soils from skin and hair. Alkyl sulfates and alkyl ether sulfates are ubiquitous in this role because they provide rich foam and are cost effective. A relatively minor proportion of a "secondary" surfactant is usually included to build viscosity, improve solubility, stabilize the foam, enhance foaming, or improve mildness. The most common secondary surfactants are fatty alkanolamides (e.g., cocamide MEA, lauramide MEA, or cocamide DEA), and betaines (e.g., cocamidopropyl betaine). Formulations free of cocamide MEA or cocamide DEA have become desirable to formulators to reduce irritation or to avoid the need for warnings required by certain government regulations such as California's Proposition 65.

Fatty alkyl N,N-dialkylamides, especially $C_8$-$C_{10}$ alkyl N,N-dimethylamides, are well-known solvents. Stepan Company, for instance, sells HALLCOMID® M-10 and HALLCOMID® M-8-10 for use as solvents in industrial degreasing, coatings, and agricultural formulations. The N,N-dialkylamides are not generally used for personal care applications except as solubilizers for sunscreen actives (see, e.g., U.S. Pat. Nos. 4,506,051; 6,485,713; 7,790,146; and 8,153,105 and PCT Int. Appl. WO 2007/085568) or as components of deodorant sticks (see U.S. Pat. Appl. Publ. No. 2003/0215472). PCT Int. Appl. WO 2013/052545 teaches to use fatty alkyl N,N-dialkylamides to help solubilize apigenin in compositions used to treat hair thinning or greying. Fatty alkyl N,N-dialkylamides have been proposed as soap curd dispersants for laundry detergents (see, e.g., U.S. Pat. No. 3,843,543) or as part of a light-duty dish detergent (see U.S. Pat. No. 3,676,372). Thus, compositions comprising $C_8$-$C_{14}$ alkyl N,N-dialkylamides and intended for use as personal cleansers are apparently unknown.

Recently, monounsaturated fatty alkyl N,N-dimethylamides and monounsaturated fatty alkanolamides were tested and found to have good foaming and viscosity-building properties (see PCT Int. Appl. No. WO 2012/061094).

A desirable surfactant or blend will be sensitive to the amount of added viscosity modifier. Usually, a salt (e.g., sodium chloride) is added to increase viscosity. Preferably, the amount of added salt needed to achieve a favorable viscosity profile is minimized. However, with many primary anionic surfactants (e.g., alpha-olefin sulfonates, alkyl ether sulfates, fatty sulfosuccinates, fatty sulfoacetates, and their mixtures), building viscosity with the popular alkanolamides or betaines can be difficult or may require a relatively high proportion of salt.

Good surfactants are not necessarily good solubilizers. This is a particular concern in personal cleansers because the industry uses a wide variety of fragrances, essential oils, and other components having diverse chemical structures. Many of these materials are hydrophobic and difficult to solubilize in a highly aqueous mixture.

Still needed are surfactants or surfactant blends that can deliver good foaming, mildness, and an improved viscosity build profile to personal cleansers. Liquid surfactants or blends, particularly products that can be formulated at high actives levels, are also needed. Particularly valuable are surfactants or blends that could be formulated at any actives level up to 100% actives. Surfactants or blends having the ability to solubilize cleanser components, including a wider variety of fragrances and high levels of fragrances (e.g., >2 wt. %), are also needed. In addition, the industry would benefit from the availability of MEA or DEA-free formulations that build viscosity readily with even challenging anionic surfactants.

SUMMARY OF THE INVENTION

In one aspect, the invention relates to a personal cleanser. The cleanser comprises 5 to 98 wt. % of a primary anionic surfactant, 0.1 to 30 wt. % of a saturated $C_8$-$C_{14}$ alkyl N,N-dialkylamide, and water. The invention includes surfactant blends comprising a primary anionic surfactant and the saturated $C_8$-$C_{14}$ alkyl N,N-dialkylamide.

In another aspect, the personal cleanser comprises 1 to 75 wt. % of a primary anionic surfactant, 0.1 to 20 wt. % of a saturated $C_8$-$C_{14}$ alkyl N,N-dialkylamide, 0.1 to 50 wt. % of a moisturizing oil, and water.

In another aspect, the personal cleanser comprises 5 to 98 wt. % of a primary anionic surfactant, 0.1 to 30 wt. % of a saturated $C_8$-$C_{14}$ alkyl N,N-dialkylamide, 0.1 to 5 wt. % of a fragrance, and water.

We surprisingly found that personal cleansers that incorporate a saturated $C_8$-$C_{14}$ alkyl N,N-dialkylamide as a secondary surfactant have good foaming properties and improved viscosity profiles compared with cleansers that rely on alkanolamides or betaines as the secondary surfactant. The saturated $C_8$-$C_{14}$ alkyl N,N-dialkylamides are water-white liquids that solubilize cleanser components and can be formulated easily without heating at any actives level up to 100%. The surfactant blends avoid the need to use an alkanolamide surfactant. Importantly, the surfactant blends build viscosity with less added salt compared with the alkanolamide or betaine-based blends currently used to formulate personal cleansers. In fact, the fatty N,N-dialkylamides build viscosity readily even with challenging primary anionic surfactants, i.e., ones that resist viscosity build with alkanolamides, such as olefin sulfonates or relatively mild primary anionic surfactants.

Fatty N,N-dialkylamides are excellent solubilizers for fragrances, essential oils, and other hydrophobic cleanser components, and they readily combine with emollients to give stable emulsions useful for cosmetics, face creams, lotions, and other skin-care products. Cleansers comprising the moisturizing oils have excellent flash foaming character, foam volume, and foam feel and provide a luxurious, lotion-like after-feel. The inventive personal cleansers include, for example, shampoos, body washes, facial cleansers, shower gels, liquid soaps, hand soaps, baby liquid cleansers, pet shampoos, and bubble baths.

DETAILED DESCRIPTION OF THE INVENTION

Personal cleansers of the invention comprise a primary anionic surfactant, a saturated $C_8$-$C_{14}$ alkyl N,N-dialkylamide, and water. The personal cleansers may incorporate additional surfactants, additives, or other components depending on the particular type of formulation. The personal cleansers include shampoos, body washes, facial cleansers, shower gels, liquid soaps, hand soaps, baby liquid cleansers, pet shampoos, bubble baths, and the like.

In some aspects, the inventive personal cleansers comprise 5 to 98 wt. %, preferably 15 to 90 wt. %, most preferably 20 to 60 wt. %, of a primary anionic surfactant.

Suitable anionic surfactants are well known, and a wide variety of these are considered useful for personal cleansing. Suitable anionic surfactants for use in the cleansers and surfactant blends include, for example, alkyl sulfates (e.g., ammonium lauryl sulfate, sodium lauryl sulfate, sodium coco sulfate), alkyl ether sulfates (e.g., sodium laureth sulfates having 1-3 moles of EO, such as STEOL® CS-170, STEOL® CS-230, or STEOL® CS-330), alpha olefin sulfonates (e.g., BIO-TERGE® AS-40, a sodium $C_{14}$-$C_{16}$ olefin sulfonate), paraffin sulfonates, alkyl benzene sulfonates (e.g., BIO-SOFT® N-300, a TEA dodecylbenzene sulfonate), alpha sulfo methyl esters, alkyl sulfoacetates and alkyl ether sulfoacetates (e.g. LANTHANOL® LAL, a sodium lauryl sulfoacetate), alkyl sulfosuccinates and alkyl ether sulfosuccinates (e.g., STEPAN-MILD® LSB, a blend of sodium lauryl sulfoacetate and disodium laureth sulfocuccinate), sulfolaurates (e.g., ALPHA-STEP® PC-48, a mixture of sodium methyl 2-sulfolaurate and disodium 2-sulfolaurate), propionates, amphoacetates, sarcosinates, alkyl phosphates, alkyl ether phosphates, alkyl ether carboxylates, acyl lactylates, acyl glycinates, alkyl isethionates, alkyl taurates, and the like, and mixtures thereof. Preferably, the anionic surfactant is selected from alkyl sulfates, alkyl ether sulfates, alpha olefin sulfonates, alkyl sulfoacetates, alkyl ether sulfoacetates, alkyl sulfosuccinates, alkyl ether sulfosuccinates, and mixtures thereof. For specific examples of additional suitable primary anionic surfactants, see U.S. Pat. No. 8,053,400 and U.S. Pat. Appl. Publ. No. 2010/0183539, the teachings of which are incorporated herein by reference.

The personal cleansers comprise 0.1 to 30 wt. %, preferably 0.5 to 25 wt. %, and most preferably 1 to 10 wt. % of a saturated $C_8$-$C_{14}$ alkyl N,N-dialkylamide.

Suitable saturated $C_8$-$C_{14}$ alkyl N,N-dialkylamides, also referred to herein as "fatty N,N-dialkylamides," have a linear or branched, preferably linear, chain comprising 8 to 14 carbons. Suitable fatty N,N-dialkylamides are conveniently prepared by reacting the corresponding fatty carboxylic acid or acid derivative (preferably an ester) with a secondary amine. In some cases, the fatty carboxylic acid derivative may be a triglyceride, although it is more typically a lower alkyl ester, such as a methyl ester. The N,N-dialkylamides preferably derive from $C_2$-$C_8$ secondary amines such as dimethylamine, diethylamine, diisopropylamine, and the like. Typically, the fatty ester precursor is reacted with dimethylamine or diethylamine, usually in the presence of a base such as an alkoxide, to give the corresponding fatty N,N-dimethylamide or fatty N,N-diethylamide. Fatty N,N-dimethylamides are most preferred.

The $C_8$-$C_{14}$ alkyl N,N-dialkylamide may comprise individual components (e.g., a straight $C_{12}$ dialkylamide or a straight $C_{14}$ dialkylamide), or it may comprise any mixture of components within the $C_8$-$C_{14}$ range (e.g., a mixture of $C_8$ and $C_{10}$ dialkylamides or a mixture of $C_{12}$ and $C_{14}$ dialkylamides).

N,N-Dimethyllauramide, a saturated $C_{12}$ alkyl dimethylamide, is commercially available from Stepan Company as HALLCOMID® M-12. N,N-Dimethylcocamide, a saturated $C_{12}$-$C_{14}$ alkyl N,N-dimethylamide mixture derived from coco methyl esters, is also available from Stepan as HALLCOMID® M-12-14. As shown in the examples below, these materials perform exceptionally well as secondary surfactants in personal cleansers. Also available from Stepan are HALLCOMID® M-8-10, a mixture of N,N-dimethylcaprylamide and N,N-dimethylcapramide, and HALLCOMID® M-10, which is N,N-dimethylcapramide.

The saturated $C_8$-$C_{14}$ alkyl N,N-dialkylamides are water-white liquids that can be formulated easily without heating at any actives level up to 100%. This is a substantial handling advantage, as high-actives formulations may be unobtainable with other secondary surfactants. The N,N-dialkylamides are also excellent solubilizers for fragrances, essential oils, and other hydrophobic cleanser components. Use of the $C_8$-$C_{14}$ alkyl N,N-dialkylamides as secondary surfactants may also avoid the need to use an alkanolamide surfactant. This may be desirable or important for meeting increasingly strict government standards, such as California's Proposition 65.

The primary anionic surfactant and the saturated $C_8$-$C_{14}$ alkyl N,N-dialkylamide can be used in any desired weight ratio, and the amounts used will depend on the nature of the anionic surfactant, the nature of the fatty N,N-dialkylamide, the particular personal cleanser application, and other factors. Usually, a major proportion of the primary anionic surfactant is used. In one preferred aspect, the weight ratio of the primary anionic surfactant to the fatty N,N-dialkylamide is within the range of 50:1 to 2:1, more preferably from 10:1 to 3:1.

The personal cleansers also comprise water, which makes up the balance of the formulation except for additional surfactants or other additives that might be included in addition to the primary anionic surfactant and the saturated $C_8$-$C_{14}$ alkyl N,N-dialkylamide. The amount of water present will vary depending upon whether the personal cleanser is in a concentrated or dilute formula. For instance, the cleanser might have as much as 95 wt. % or as little as 1 wt. % of water. Typically, the amount of water in the personal cleanser will range from 10 to 90 wt. %, more typically 25 to 75 wt. %, and preferably 45 to 65 wt. %.

Additional surfactants may be included in the inventive personal cleansers. Suitable additional surfactants include cationic, amphoteric, zwitterionic, and nonionic surfactants. Suitable cationic surfactants include, for example, alkyldimethylammonium halides, quaternized cellulose, esterquats, amidoquats, stearylamidopropyl dimethylamine quats, and the like. For additional examples, see U.S. Pat. No. 4,228,044, the teachings of which are incorporated herein by reference. Suitable amphoteric surfactants include amine oxides, betaines, sultaines, sulfobetaines, and the like. Examples include lauramine oxide, myristylamine oxide, cocamine oxide (available as the AMMONYX® amine oxides from Stepan), cocamidopropyl betaine, laurylamidopropyl betaine, and cocamidopropyl hydroxysultaine (available as the AMPHOSOL® products from Stepan). Suitable nonionic surfactants include alkanolamides and ethoxylated alkanolamides (e.g., cocamide MEA, cocamide DEA, lauramide DEA, lauramide MEA, such as NINOL® COMF, NINOL® 30-LL, NINOL® C-4, and NINOL® C-5, products of Stepan), fatty alcohols, fatty alcohol ethoxylates, alkylpolyglycosides, alkylphenol ethoxylates, and the like. For additional examples of suitable additional surfactants, see U.S. Pat. No. 8,053,400 and U.S. Pat. Appl. Publ. No. 2010/0183539, the teachings of which are incorporated herein by reference.

In some aspects, a moisturizing oil is included in the personal cleanser. Moisturizing oils are commonly included in body washes, facial cleansers, shower gels, liquid soaps, hand soaps, bubble baths, and other similar personal cleansers. Suitable moisturizing oils are well known in the art. They include, for example, natural oils (e.g., soybean oil, olive oil, grapeseed oil, sunflower oil), petrolatum, and the like.

The personal cleansers may include one or more other additives. Suitable additives include humectants, viscosity modifiers, pH adjusters, foam stabilizers, preservatives, dyes, thickeners, skin-feel enhancers, conditioners, antibacterial agents, detergents, builders, proteins, vitamins, emollients, and the like. For examples of these conventional components, see U.S. Pat. No. 8,053,400, the teachings of which are incorporated herein by reference.

The inventive personal cleansers exhibit good foaming properties that are comparable to those normally seen when alkanolamides or betaines are used as the secondary surfactant. Tables 1-4 show that long-lasting foams with good volume are generally observed with or without castor oil present, particularly when a saturated $C_{12}$-$C_{14}$ alkyl N,N-dialkylamide is used as a secondary surfactant.

We surprisingly found that personal cleansers that incorporate a saturated $C_8$-$C_{14}$ alkyl N,N-dialkylamide as a secondary surfactant have improved viscosity profiles compared with cleansers that rely on alkanolamides or betaines. The surfactant blends build viscosity readily even with challenging primary anionic surfactants, i.e., ones that resist viscosity build with alkanolamides, such as olefin sulfonates or relatively mild primary anionic surfactants. As shown in Tables 1-4, the identity of the primary anionic surfactant is relatively unimportant. When a saturated $C_{12}$-$C_{14}$ alkyl N,N-dialkylamide is used as a secondary surfactant, viscosity builds very rapidly when sodium chloride is added. This will allow formulators to reduce the amount of salt needed to achieve a desirably high viscosity. Moreover, the saturated $C_{12}$-$C_{14}$ alkyl N,N-dialkylamides also build viscosity much more readily than even the monounsaturated analog, C12-25, a material now available because of recent improvements in metathesis chemistry (see WO 2012/061094).

Thus, in one aspect, the invention is a personal cleanser that utilizes a saturated $C_8$-$C_{14}$ alkyl N,N-dialkylamide, preferably a saturated $C_{12}$-$C_{14}$ alkyl N,N-dialkylamide, as a secondary surfactant and has an improved viscosity build profile as a function of wt. % added sodium chloride compared with a similar cleanser formulated using the same anionic surfactant and cocamide MEA or cocamidopropyl betaine. In another aspect, the invention is a personal cleanser that utilizes a saturated $C_8$-$C_{14}$ alkyl N,N-dialkylamide, preferably a saturated $C_{12}$-$C_{14}$ alkyl N,N-dialkylamide, as a secondary surfactant and has an improved viscosity build profile as a function of wt. % added sodium chloride compared with a similar cleanser formulated using the same anionic surfactant and a monounsaturated $C_{12}$ alkyl N,N-dimethylamide or monounsaturated $C_{12}$ alkyl MEA amide.

In another aspect, the invention relates to a surfactant blend useful in personal cleansing applications. The blend comprises a primary anionic surfactant and a saturated $C_8$-$C_{14}$ alkyl N,N-dialkylamide. The blends typically comprise a major proportion of the anionic surfactant and a minor proportion of the saturated $C_8$-$C_{14}$ alkyl N,N-dialkylamide. Preferably, the weight ratio of the primary anionic surfactant to the fatty N,N-dialkylamide in the surfactant blend is within the range of 50:1 to 2:1, more preferably from 10:1 to 3:1.

In another aspect, the invention relates to personal cleansers comprising a moisturizing oil. Such personal cleansers comprise 1 to 75 wt. % of a primary anionic surfactant, 0.1 to 20 wt. % of a saturated $C_8$-$C_{14}$ alkyl N,N-dialkylamide, 0.1 to 50 wt. % of a moisturizing oil, and water. Preferred cleansers of this type comprise 3 to 70 wt. % of the primary anionic surfactant, 1 to 15 wt. % of a betaine surfactant (such as cocamidopropyl betaine), 1 to 10 wt. % of a saturated $C_{12}$-$C_{14}$ alkyl N,N-dialkylamide, 3 to 40 wt. % of the moisturizing oil, and water. Personal cleansers that include a moisturizing oil may be body washes, facial cleansers, shower gels, liquid soaps, hand soaps, bubble baths, or similar products. Suitable anionic surfactants for these cleansers have already been described. Preferably, the fatty N,N-dialkylamide is a $C_{12}$-$C_{14}$ alkyl N,N-dimethylamide. Preferred moisturizing oils are natural oils (soybean oil, olive oil, grapeseed oil, sunflower oil, or the like) and petrolatum.

The saturated $C_8$-$C_{14}$ alkyl N,N-dialkylamides make it possible to formulate moisturizing cleansers with excellent flash foaming character, foam volume, and foam feel. The cleansers also provide a luxurious, lotion-like after-feel. The saturated $C_8$-$C_{14}$ alkyl N,N-dialkylamides allow room-temperature preparation of stable emulsions containing 5-20 wt. % oil. When tested at elevated temperature, a formulation with 10 wt. % soybean oil and HALLCOMID® M-12-14 is stable for at least 4 weeks at 45° C. (see Tables 5-6).

In another aspect, the invention relates to oil-in-water emulsions. Such emulsions are useful for a variety of personal care applications, including cosmetics, face creams, lotions, and other skin-care products. The emulsions comprise: (a) a continuous aqueous phase; and (b) a discontinuous phase comprising one or more emollients and 0.1 to 35 wt. %, based on the amount of emulsion, of a saturated $C_8$-$C_{14}$ alkyl N,N-dialkylamide. Preferably, the emulsion comprises 30 to 98 wt. % of water, more preferably 50 to 95 wt. % of water.

Suitable emollients for use in the oil-in-water emulsions are well known in the art, and include natural oils or other triglycerides, fatty esters, fatty alcohols, fatty carbonates, fatty acids, mineral oils, wax esters, glycols, and the like, and mixtures thereof. Specific examples of suitable emollients include isopropyl myristate, isopropyl palmitate, cetyl palmitate, polyoxypropylene stearyl ethers, octyl stearate, isooctyl stearate, 2-ethylhexyl palmitate, fatty alcohol benzoates, lanolin, lanolin alcohol, sterol fatty esters, dimethicone, allantoin, and the like, and mixtures thereof.

The oil-in-water emulsions can include other components, including thickeners, emulsifiers (e.g., glyceryl monostearate, cetyl alcohol, or the like), humectants (e.g., glycerin, propylene glycol, urea), botanical extracts (e.g., aloe), and the like.

The amount of emollient in the emulsion depends on the nature of emollient(s), the intended application for the emulsion, and other factors. Generally, however, it is preferred to prepare emulsions comprising 2 to 30 wt. %, more preferably 5 to 25 wt. %, most preferably 10 to 15 wt. % of the emollient. The emulsion preferably comprises 0.5 to 20 wt. %, more preferably 1 to 10 wt. %, of the saturated $C_8$-$C_{14}$ alkyl N,N-dialkylamide. The preparation of an inventive oil-in-water emulsion comprising HALLCOMID® M-12-14 is illustrated in examples below.

In some aspects, the discontinuous phase of the emulsion further comprises a solubilized active ingredient. Suitable active ingredients are selected vitamins, minerals, carrier oils, essential oils, pigments, exfoliants, polyunsaturated fatty acids, anti-aging agents, wrinkle-reduction agents, fragrances, and the like, and mixtures thereof.

In another aspect, the invention relates to personal cleansers that incorporate a fragrance, which may be present in a relatively high percentage. Thus, some inventive personal cleansers comprise 5 to 98 wt. % of a primary anionic surfactant, 0.1 to 30 wt. % of a saturated $C_8$-$C_{14}$ alkyl N,N-dialkylamide, 0.1 to 5 wt. % of a fragrance, and water.

In some aspects, the fatty N,N-dialkylamide is a saturated $C_8$-$C_{12}$ alkyl N,N-dialkylamide, preferably an N,N-dimethylamide. In other aspects, N,N-dialkylamide is a saturated $C_8$-$C_{10}$ alkyl N,N-dialkylamide, preferably an N,N-dimethylamide.

In one preferred aspect, the personal cleanser comprises 20 to 60 wt. % of the anionic surfactant, 1 to 10 wt. % of the $C_8$-$C_{14}$ alkyl N,N-dialkylamide, and 2 to 5 wt. % of the fragrance.

Suitable fragrances are well known and come in a wide variety of scents, including, among others: floral, citrus, fruity, green, oceanic, oriental, spicy, and woody. Each category includes a bewilderingly diverse array of chemical structures and compositions, and they are often mixtures of multiple components.

Most fragrances, however, have low or very low water solubility, so finding ways to formulate them into highly aqueous personal cleansers poses a considerable challenge. This is especially true of formulations for which a large proportion (e.g., 2-5 wt. %) of fragrance is desirable. High fragrance levels are achievable by including ethoxylated surfactants such as polyoxyethylene sorbitan laurate or the like in the formulation. However, many formulators want to avoid ethoxylated surfactants and seek other ways to incorporate high fragrance levels into personal cleansers.

The use of high fragrance levels and the market push to include more natural materials in personal cleansers also makes it challenging for formulators to build viscosity, and to do so without including an excessive amount of salt.

Thus, in one aspect, the inventive personal cleansers have 0.1 to 5 wt. % of the fragrance, and they can have relatively high levels of fragrance such as 1 to 5 wt. %, 2 to 5 wt. %, or 3 to 4 wt. %.

In a preferred aspect, the personal cleanser is clear and homogeneous, and preferably comprises 1 to 5 wt. % of the fragrance.

In another preferred aspect, the personal cleanser further comprises a solubilized active ingredient. Suitable solubilized active ingredients are selected vitamins, minerals, carrier oils, essential oils, pigments, exfoliants, polyunsaturated fatty acids, anti-aging agents, wrinkle-reduction agents, and the like, and mixtures thereof.

The fragrance-containing personal cleanser described above can be a shampoo, body wash, facial cleanser, shower gel, liquid soap, hand soap, baby liquid cleanser, pet shampoo, bubble bath, or the like.

The following examples merely illustrate the invention. Those skilled in the art will recognize many variations that are within the spirit of the invention and scope of the claims.

Formulation Components:
Primary Anionic Surfactants (All Products of Stepan Company):
STEOL® CS-130 is sodium laureth (1 EO) sulfate (SLES)
STEOL® CS-230 is sodium laureth (2 EO) sulfate (SLES)
STEPAN-MILD® LSB is disodium laureth sulfosuccinate and sodium lauryl sulfoacetate
STEPAN-MILD® PCL is sodium methyl 2-sulfolaurate, disodium 2-sulfolaurate, and sodium lauryl sulfoacetate
STEPAN-MILD® GCC is glyceryl caprate/caprylate
BIO-TERGE® AS-40 is sodium $C_{14}$-$C_{16}$ olefin sulfonate
ALPHA-STEP® PC-48 is sodium methyl 2-sulfolaurate and disodium 2-sulfolaurate Secondary Surfactants (All Products of Stepan Company):
NINOL® COMF is cocamide monoethanolamine (cocamide MEA)
NINOL® 30LL is lauramide diethanolamine (lauramide DEA)
NINOL® M10 is cocamide monoisopropanolamine (cocamide MIPA)
AMPHOSOL® HCG is cocamidopropyl betaine
HALLCOMID® M-8-10 is N,N-dimethyl caprylamide/N,N-dimethyl capramide mixture
HALLCOMID® M-10 is N,N-dimethyl capramide
HALLCOMID® M-12 is N,N-dimethyl lauramide
HALLCOMID® M-12-14 is N,N-dimethyl cocamide
C12-30 is a monounsaturated $C_{12}$ amide based on monoethanolamine (see WO 2012/061094)
C12-25 is a monounsaturated $C_{12}$ amide based on dimethylamine (see WO 2012/061094)

Preparation of N,N-Dimethyl Lauramide

The N,N-dimethylamide is prepared by reacting methyl laurate with a slight excess of dimethylamine in the presence of an alkoxide catalyst according to generally known methods (see, e.g., U.S. Pat. No. 3,417,114). The reaction product is isolated, washed with water, and distilled to give N,N-dimethyl lauramide.

Preparation of N,N-Dimethyl Cocamide

The procedure used to make N,N-dimethyl lauramide is generally followed, except that coco methyl ester (a mixture of saturated $C_{12}$ and $C_{14}$ methyl esters) is reacted with dimethylamine. The reaction product is isolated, washed with water, and distilled to give N,N-dimethyl cocamide.

Cleansing Application

Viscosity and mechanical shake foam tests are used to assess the likely value of a particular surfactant as a secondary surfactant in cleansing applications for personal care. HALLCOMID® M-12 (N,N-dimethyl lauramide) and HALLCOMID® M-12-14 (N,N-dimethyl cocamide) are evaluated for their performance versus two controls: NINOL® COMF (cocamide MEA) and AMPHOSOL® HCG (cocamidopropyl betaine), products of Stepan Company. Two additional compositions are included as comparative secondary surfactants. They are "C12-30," a metathesis-based monounsaturated $C_{12}$ amide based on monoethanolamine and "C12-25," a metathesis-based monounsaturated $C_{12}$ amide based on dimethylamine (see WO 2012/061094).

Three different primary anionic surfactants are used. In a first series of experiments, the primary anionic surfactant is STEOL® CS-230 (sodium lauryl ether sulfate), a product of Stepan, which is used at a 12:3 weight ratio with the secondary surfactant (control or experimental sample). In a second set of experiments, the primary anionic surfactant is STEPAN-MILD® LSB, a mixture of sodium lauryl sulfoacetate and disodium laureth sulfosuccinate. Here, the weight ratios are 12:3 (anionic to secondary) for the controls and 12:1.5 for the experimental samples. In a third set of experiments, the primary anionic surfactant is BIO-TERGE® AS-40 (sodium $C_{14}$-$C_{16}$ olefin sulfonate), which is used at the 12:3 weight ratio.

Additional experiments utilize BIO-TERGE® AS-40 as the primary anionic surfactant in a liquid hand soap formulation (12:4 weight ratio with the secondary surfactant). The control secondary surfactant is NINOL® 30LL (lauramide DEA).

Viscosity curves are generated by preparing dilute aqueous solutions of the test material or control (1.5 to 3.0% active content) with 12% of the primary anionic surfactant, then measuring viscosity by means of a Brookfield DV-1+ viscometer. Sodium chloride is added incrementally (0.5 to 2 wt. %) and viscosity is recorded as a function of increasing NaCl concentration. A desirable secondary surfactant builds viscosity at least as well as the control sample. Results appear in Tables 1-4.

Foaming properties are evaluated using a mechanical shake foam test. Aqueous solutions composed of 12% active primary anionic surfactant and the test material or control (1.5% to 3.0 wt. % actives) are prepared. Sample solutions calculated at 0.2% total surfactant active material are thereafter made from the aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to settle for 15 s. Foam height is recorded. After 5 min., foam height is recorded again. The experiment is repeated without the castor oil. Test samples should provide a foam height that is within +/−25 mL of the control runs, with a superior formulation producing a foam height >25 mL greater than that of the control. Results appear in Tables 1-4.

TABLE 1

Viscosity and Foaming Properties: STEOL ® CS-230 as Primary Anionic Surfactant (12:3 with secondary surfactant)

| NaCl, wt. % | M-12-14 | NINOL ® COMF | AMPHOSOL ® HCG | C12-30 | C12-25 |
|---|---|---|---|---|---|
| | | | Viscosity, cP | | |
| 0.5 | 12,800 | 0 | 130 | 600 | 1,800 |
| 1.0 | 32,350 | 50 | 3,000 | 7,500 | 13,400 |
| 1.5 | 1,300 | 710 | 28,000 | 20,350 | 4,500 |
| 2.0 | — | 6,140 | 38.000 | 19,000 | — |
| | | | Foam height, mm | | |
| 0 min, no oil | 375 | 275 | 420 | 375 | 385 |
| 0 min, oil | 325 | 150 | 300 | 300 | 325 |
| 5 min, no oil | 375 | 275 | 420 | 375 | 385 |
| 5 min, oil | 325 | 150 | 300 | 300 | 325 |

Conclusion: HALLCOMID ® M-12-14 provides good foaming properties and a superior viscosity build profile when compared with NINOL ® COMF, AMPHOSOL ® HCG, the monounsaturated $C_{12}$ MEA amide (C12-30), or the monounsaturated $C_{12}$ DMA amide (C12-25).

TABLE 2

Viscosity and Foaming Properties: STEPAN-MILD ® LSB as Primary Anionic Surfactant (12:3 or 12:1.5 with secondary surfactant)

| NaCl, wt. % | M-12 | M-12-14 | NINOL ® COMF | C12-30 | C12-25 |
|---|---|---|---|---|---|
| | | | Viscosity, cP | | |
| 0.5 | 3,160 | 600 | 0 | 50 | 200 |
| 1.0 | 5,630 | 7,380 | 30 | 200 | 1,300 |
| 1.5 | 740 | 3,300 | 150 | 850 | 5,400 |
| 2.0 | — | — | 600 | 4,500 | 8,200 |
| | | | Foam height, mm | | |
| 0 min, no oil | 395 | 395 | 350 | 385 | 380 |
| 0 min, oil | 325 | 320 | 330 | 325 | 350 |
| 5 min, no oil | 390 | 390 | 350 | 385 | 380 |
| 5 min, oil | 325 | 320 | 330 | 325 | 350 |

Conclusion: HALLCOMID ® M-12 and M-12-14 provide good foaming properties and a superior viscosity build profile when compared with NINOL ® COMF, the monounsaturated $C_{12}$ MEA amide (C12-30), or the monounsaturated $C_{12}$ DMA amide (C12-25). HALLCOMID ® M-12 and M-12-14 are used at the 1.5 to 12 weight ratio with the primary anionic surfactant.

TABLE 3

Viscosity and Foaming Properties: BIO-TERGE ® AS-40 as Primary Anionic Surfactant (12:3 with secondary surfactant)

| NaCl, wt. % | M-12 | M-12-14 | NINOL ® COMF | AMPHOSOL ® HCG | C12-30 |
|---|---|---|---|---|---|
| | | | Viscosity, cP | | |
| 0.5 | 1,000 | 1,000 | 0 | 0 | 0 |
| 1.0 | 5,000 | 6,000 | 0 | 0 | 0 |
| 1.5 | 13,000 | 18,000 | 0 | 0 | 0 |
| 2.0 | 7,000 | 12,500 | 2,000 | 0 | — |
| | | | Foam height, mm | | |
| 0 min, no oil | 280 | 290 | 395 | 390 | 375 |
| 0 min, oil | 160 | 170 | 245 | 240 | 250 |
| 5 min, no oil | 280 | 290 | 395 | 390 | 375 |
| 5 min, oil | 160 | 170 | 295 | 240 | 250 |

Conclusion: HALLCOMID ® M-12 and M-12-14 provide good foaming properties and a superior viscosity build profile when compared with NINOL ® COMF, AMPHOSOL ® HCG, or the monounsaturated $C_{12}$ MEA amide (C12-30).

TABLE 4

Viscosity and Foaming Properties: BIO-TERGE ® AS-40 as Primary Anionic Surfactant (12:4 with secondary surfactant) in a liquid hand soap formulation

| NaCl, wt. % | M-12 | M-12-14 | NINOL ® 30LL | C12-25 (2%) |
|---|---|---|---|---|
| | | Viscosity, cP | | |
| 0.5 | 23,000 | 25,700 | 0 | 1,000 |
| 1.0 | 400 | 900 | 240 | 5,000 |
| 1.5 | — | — | 3,000 | 4,070 |
| 2.0 | — | — | 17,000 | — |
| | | Foam height, mm | | |
| 0 min, no oil | 365 | 360 | 350 | 360 |
| 0 min, oil | 255 | 290 | 200 | 275 |
| 5 min, no oil | 365 | 360 | 350 | 360 |
| 5 min, oil | 255 | 290 | 200 | 275 |

Conclusion: HALLCOMID ® M-12 and M-12-14 provide good foaming properties and a superior viscosity build profile when compared with NINOL ® 30LL (lauramide DEA) or the monounsaturated $C_{12}$ DMA amide (C12-25).

Evaluation of Emulsification Properties of Personal Cleansers Formulated with Saturated $C_{12}$-$C_{14}$ Dialkylamides Moisturizing personal cleanser formulations comprising a primary anionic surfactant, an amphoteric surfactant (AMPHOSOL® HCG), HALLCOMID® M-12-14, and soybean oil or petrolatum are prepared to evaluate the emulsifying properties of HALLCOMID® M-12-14 when combined with various anionic surfactants or their mixtures. The anionic surfactants tested include STEOL® CS-130, STEOL® CS-230, BIO-TERGE® AS-40, ALPHA-STEP® PC-48, STEPAN-MILD® LSB, STEPAN-MILD® PCL, and STEPAN-MILD® GCC (all Stepan products). Exemplary formulation details appear in Table 5.

All of the formulations tested demonstrate excellent performance in terms of their flash foaming character, foam volume, foam feel. Additionally, all of the formulations provide a luxurious, "lotion-like" after-feel. Formulations A-F have a milky appearance and flow properties. Addition of STEPAN-MILD® GCC in formulations G-J enhances the viscosity.

TABLE 5

Moisturizing Oil-Containing Personal Cleanser Formulations

| Formulation (wt. %) | A | B | C | D | E | F | G | H | I | J |
|---|---|---|---|---|---|---|---|---|---|---|
| STEPAN-MILD ® PCL | 55 | 55 | 55 | | | | | | 55 | 55 |
| STEOL ® CS-130 | | | | 43 | 43 | 43 | | | | |
| STEOL ® CS-230 | | | | | | | 48 | 48 | | |
| STEPAN-MILD ® GCC | | | | | | | 2 | 2 | 2 | 2 |
| AMPHOSOL ® HCG | 9.6 | 9.6 | 9.6 | 9.6 | 9.6 | 9.6 | 9.6 | 9.6 | 9.6 | 9.6 |
| HALLCOMID ® M-12-14 | 3 | 3 | 3 | 3 | 3 | 3 | 3 | 3 | 3 | 3 |
| Soybean oil | 5 | 10 | | 5 | 10 | | 10 | | 20 | |
| Petrolatum | | | 5 | | | 5 | | 10 | | 20 |
| Deionized water | q.s. | q.s. | q.s. | q.s. | q.s. | q.s. | q.s. | q.s. | q.s. | q.s. |

Emulsification Property and Emulsion Stability

Saturated and unsaturated fatty amides are compared for their ability to emulsify high levels of oils (fatty acids and triglyceride-based vegetable oils such as soybean oil or sunflower seed oil) at room temperature and provide stable emulsions.

Tested Formulations:

Formulations with 10% oil (wt. %): STEPAN-MILD® PCL (55); AMPHOSOL® HCG (9.6); STEPAN-MILD® GCC (2.0); saturated or unsaturated fatty amide (3.0); soybean oil (10.0); deionized water (20.4).

Formulations with 20% oil (wt. %): STEPAN-MILD® PCL (55); AMPHOSOL® HCG (9.6); STEPAN-MILD® GCC (2.0); saturated or unsaturated fatty amide (3.0); soybean oil (20.0); deionized water (10.4).

Control formulation: STEPAN-MILD® PCL (55); AMPHOSOL® HCG (9.6); NINOL® M10 (cocamide MIPA) (3.0); soybean oil (10.0); deionized water (22.4).

The control formulation requires elevated temperature for its preparation because NINOL® M10 is a solid at room temperature. The formulation is stable at room temperature for four weeks, but it separates after one week at 45° C.

Table 6 provides emulsion stability results from the test formulations. As shown in the table, HALLCOMID® M-12 and HALLCOMID® M-12-14, the saturated dimethyl amides, generally provide a higher level of emulsion stability at 10 wt. % oil when compared with the unsaturated $C_{12}$ alkyl dimethyl amide (C12-25) and unsaturated $C_{12}$ alkyl MEA amide (C12-30). Additionally, HALLCOMID® M-12 and HALLCOMID® M-12-14 demonstrate good emulsion stability even at 20 wt. % oil.

When tested at elevated temperature, the formulation with 10 wt. % soybean oil and HALLCOMID® M-12-14 is stable for at least 4 weeks at 45° C.

TABLE 6

Evaluation of Emulsion Stability

| | Stability, room temperature | | | | 45° C. | |
|---|---|---|---|---|---|---|
| | 1 wk | 2 wks | 3 wks | 4 wks | 1 wk | 4 wks |
| HALLCOMID ® M-12 + 10% petrolatum | yes | yes | yes | yes | — | — |
| HALLCOMID ® M-12 + 10% soybean oil | yes | yes | yes | yes | — | — |
| HALLCOMID ® M-12-14 + 10% soybean oil | yes | yes | yes | yes | yes | yes |
| HALLCOMID ® M-12-14 + 20% petrolatum | yes | yes | yes | yes | — | — |
| HALLCOMID ® M-12-14 + 20% soybean oil | yes | yes | yes | yes | — | — |
| Cocamide MIPA + 10% soybean oil (control) | yes | yes | yes | yes | no | no |
| C12-25 + 10% petrolatum | yes | yes | yes | yes | — | — |
| C12-25 + 10% soybean oil | yes | no | no | no | — | — |
| C12-30 + 10% petrolatum | yes | no | no | no | — | — |
| C12-30 + 10% soybean oil | yes | yes | yes | yes | — | — |

Oil-in-Water Emulsions

Comparative Formulation K (wt. %): HallStar® IPM (10); HallStar® cetyl alcohol (3.0); HallStar® GMS pure (2.0), deionized water (q.s. to 100); preservative, color, dye (q.s.); citric acid (q.s.); sodium hydroxide (q.s.).

Formulation L (wt. %): Same as Comparative Formulation K, with 3 wt. % of HALLCOMID® M-12-14 added.

Procedure:

A vessel is charged with deionized water, which is mixed and heated to 170-175° F. (77 to 79° C.). In a separate container, the HallStar® IPM (isopropyl myristate), HALLCOMID® M-12-14, cetyl alcohol, and HallStar® GMS (glyceryl monostearate) are combined and heated to 170-175° F. The agitation rate of the water phase is increased, and the oil phase is slowly added. After 5 min. of additional mixing, the pH is adjusted to 5.5 to 6.5, and the mixture is emulsified for 20-25 min. The mixture is cooled to 80° F. (27° C.), and preservative, color, and/or dye are added if desired. The pH is adjusted with citric acid or sodium hydroxide as needed.

Results:

Comparative Formulation K separates within 1 day. Formulation L (with the HALLCOMID® M-12-14) is stable for 3 weeks. Thus, HALLCOMID® M-12-14 works well as an emulsifier for the preparation of oil-in-water emulsions.

Fragrance Solubilization

Examples M, N, P, and Q below illustrate the ability of fatty N,N-dialkylamides to function as fragrance solubilizers for personal care applications. Each of the formulations contains a relatively high percentage (3.0 wt. %) of fragrance. Many fragrances have very low water solubility and can be used only at low levels (e.g., 1 wt. % or less) without causing phase separation. We surprisingly found (see Table 7) that a high concentration of fragrance can be tolerated when fatty N,N-dialkylamides are included in aqueous personal care formulations with a primary anionic surfactant. As shown in the table, clear products can be obtained with HALLCOMID® M-10 or HALLCOMID® M-12 with the Fragrance #2. Although Fragrance #1 proved more challenging, it gives a clear product with HALLCOMID® M-8-10.

TABLE 7

Fragrance Solubilization using Fatty N,N-Dialkylamides

| Formulation (wt. %) | M | N | P | Q |
|---|---|---|---|---|
| STEOL ® CS-230 | 48 | 48 | 48 | 48 |
| AMPHOSOL ® HCG | 9.6 | 9.6 | 9.6 | 9.6 |
| HALLCOMID ® M-8-10 | 3.0 | — | — | — |
| HALLCOMID ® M-12 | — | 3.0 | 3.0 | — |
| HALLCOMID ® M-10 | — | — | — | 3.0 |
| Fragrance #1 | 3.0 | 3.0 | — | — |
| Fragrance #2 | — | — | 3.0 | 3.0 |
| Deionized water | q.s. | q.s. | q.s. | q.s. |
| pH | 6.0 | 6.0 | 6.0 | 6.0 |
| Viscosity | — | — | high | low |
| Appearance | clear | opaque | clear | clear |

The preceding examples are meant only as illustrations. The following claims define the invention.

We claim:

1. A composition comprising 15 to 90 wt. % of a primary anionic surfactant selected from the group consisting of alkyl sulfates, alkyl ether sulfates, olefin sulfonates, alkyl sulfoacetates, alkyl ether sulfoacetates, alkyl sulfosuccinates, alkyl ether sulfosuccinates, and mixtures thereof, 0.5 to 25 wt. % of a saturated $C_{12}$-$C_{14}$ alkyl N,N-dialkylamide, and 10 to 90 wt. % of water, wherein the composition is suitable for use as a personal cleanser selected from the group consisting of shampoos, body washes, shower gels, facial cleansers, liquid soaps, hand soaps, moisturizing cleansers, baby liquid cleansers, pet shampoos, and bubble baths.

2. The composition of claim 1 wherein the N,N-dialkylamide is N,N-dimethyllauramide or N,N-dimethylcocamide.

3. The composition of claim 1 comprising 20 to 60 wt. % of the anionic surfactant and 1 to 10 wt. % of the $C_{12}$-$C_{14}$ alkyl N,N-dialkylamide.

4. The composition of claim 1 having an improved viscosity build profile as a function of wt. % added sodium chloride compared with a similar cleanser formulated using the same anionic surfactant and cocamide MEA or cocamidopropyl betaine.

5. The composition of claim 1 having an improved viscosity build profile as a function of wt. % added sodium chloride compared with a similar cleanser formulated using the same anionic surfactant and a monounsaturated $C_{12}$ alkyl N,N-dimethylamide or monounsaturated $C_{12}$ alkyl MEA amide.

6. The composition of claim 1 further comprising at least one additive selected from the group consisting of humectants, viscosity modifiers, pH adjusters, foam stabilizers, preservatives, dyes, thickeners, skin-feel enhancers, conditioners, anti-bacterial agents, detergents, builders, proteins, vitamins, emollients, natural oils, and moisturizers.

7. A composition comprising 3 to 70 wt. % of a primary anionic surfactant selected from the group consisting of alkyl sulfates, alkyl ether sulfates, olefin sulfonates, alkyl sulfoacetates, alkyl ether sulfoacetates, alkyl sulfosuccinates, alkyl ether sulfosuccinates, and mixtures thereof, 1 to 15 wt. % of a betaine surfactant, 1 to 10 wt. % of a saturated $C_{12}$-$C_{14}$ alkyl N,N-dialkylamide, 3 to 40 wt. % of a moisturizing oil, and water, wherein the composition is suitable for use as a personal cleanser selected from the group consisting of shampoos, body washes, shower gels, facial cleansers, liquid soaps, hand soaps, moisturizing cleansers, baby liquid cleansers, pet shampoos, and bubble baths.

8. The composition of claim 7 wherein the moisturizing oil is a natural oil or petrolatum.

9. An oil-in-water emulsion comprising:
 (a) a continuous aqueous phase comprising 30 to 98 wt. % of water; and
 (b) a discontinuous phase comprising 2 to 30 wt. %, based on the amount of emulsion, of one or more emollients selected from the group consisting of natural oils, triglycerides, fatty esters, fatty alcohols, fatty carbonates, fatty acids, mineral oils, wax esters, glycols, or mixtures thereof, and 0.5 to 20 wt. %, based on the amount of emulsion, of a saturated $C_{12}$-$C_{14}$ alkyl N,N-dialkylamide, wherein the emulsion is suitable for use as a cosmetic, face cream, lotion, or skin-care product.

10. The emulsion of claim 9 wherein the discontinuous phase further comprises a solubilized active ingredient selected from the group consisting of vitamins, minerals, carrier oils, essential oils, pigments, exfoliants, polyunsaturated fatty acids, anti-aging agents, wrinkle-reduction agents, fragrances, and mixtures thereof.

11. A composition comprising 20 to 60 wt. % of a primary anionic surfactant selected from the group consisting of alkyl sulfates, alkyl ether sulfates, olefin sulfonates, alkyl sulfoacetates, alkyl ether sulfoacetates, alkyl sulfosuccinates, alkyl ether sulfosuccinates, and mixtures thereof, 1 to 10 wt. % of a saturated $C_{12}$-$C_{14}$ alkyl N,N-dialkylamide, 2 to 5 wt. % of a fragrance, and water, wherein the composition is suitable for use as a personal cleanser selected from the group consisting of shampoos, body washes, shower gels, facial cleansers, liquid soaps, hand soaps, moisturizing cleansers, baby liquid cleansers, pet shampoos, and bubble baths.

12. The composition of claim 11 wherein the N,N-dialkylamide is a $C_{12}$-$C_{14}$ alkyl N,N-dimethylamide.

13. A clear, homogeneous composition of claim 11.

14. The composition of claim 11 comprising 3 to 4 wt. % of the fragrance.

15. The composition of claim 11 further comprising a solubilized active ingredient selected from the group consisting of vitamins, minerals, carrier oils, essential oils, pigments, exfoliants, polyunsaturated fatty acids, anti-aging agents, wrinkle-reduction agents, and mixtures thereof.

* * * * *